United States Patent [19]

Björk

[11] Patent Number: 5,013,735

[45] Date of Patent: May 7, 1991

[54] METHOD OF TREATING THERAPY-RESISTANT SCHIZOPHRENIA WITH AMPEROZIDE (N-ETHYL-4-(4',4'-BIS(P-FLUOROPHENYL)-BUTYL)-1-PIPERAZINE-CARBOXAMIDE

[75] Inventor: Anders K. Björk, Jägarevägen, Sweden

[73] Assignee: Pharmacia AB, Sweden

[21] Appl. No.: 487,547

[22] Filed: Mar. 1, 1990

[51] Int. Cl.$^5$ .................................... A61K 31/495

[52] U.S. Cl. .................................................. 514/255

[58] Field of Search ........................................ 514/255

Primary Examiner—Stanley J. Friedman
Attorney, Agent, or Firm—Pravel, Gambrell, Hewitt, Kimball & Krieger

[57] ABSTRACT

The present invention relates to a method for treating a patient suffering from therapy-resistant schizophrenia by administering to the patient a therapeutically effective amount of amperozide.

4 Claims, No Drawings

METHOD OF TREATING THERAPY-RESISTANT SCHIZOPHRENIA WITH AMPEROZIDE (N-ETHYL-4-(4',4'-BIS(P-FLUOROPHENYL)-BUTYL)-1-PIPERAZINE-CARBOXAMIDE

FIELD OF THE INVENTION

This invention relates to a method for the treatment of patients suffering from therapy-resistant schizophrenia by administration of the drug amperozide, N-ethyl-4-[4',4'-bis(p-flurophenyl)butyl]-1-piperazinecarboxamide.

BACKGROUND OF THE INVENTION

The treatment of schizophrenia remains one of the major challenges of modern day medicine. Even incremental advances in the safe and effective use of currently available treatments can have a major impact on the lives of schizophrenic individuals and their families. Reducing rates of relapse and rehospitalization by as little as ten percent per year can have enormous public health implications (J. M. Kane, *Special Report: Schizoohrenia*, 1987 National Institute of Mental Health).

It is estimated that approximately two million Americans suffer from classical schizophrenia. Approximately 200,000 to 400,000 (I0 to 20%) of these schizophrenic patients do not respond to treatment with traditional neuroleptics (antipsychotic drugs) and are classified as therapy-resistant schizophrenics.

Data gathered from maintenance medication trials indicate that 20 to 30 percent of patients initially responsive to antipsychotic drugs may relapse during the first year or two of maintenance drug treatment. A proportion of these relapsed patients may contribute to the number of patients who are refractory to treatment (J. M. Kane, J. Lieberman, *Psychopharmacology: The Third Generation of Progress*, 1987, Ed. H. Y. Meltzer).

The term "treatment resistant" or "therapy resistant" schizophrenia used in this context describes a particular illness generally understood by a physician skilled in the art. The treatment-resistant schizophrenic patient may be minimally defined as a patient with schizophrenia without marked symptomatic relief from two treatment periods each with a neuroleptic agent from a different chemical class. Clinical research has suggested that neurolepticresistant patients suffer from an illness which is characterized by pharmacodynamic, psychological, and physiological properties which differ from those of the neuroleptic-responsive patient. Thus, therapeutic agents known to be effective in the treatment of schizophrenia are not useful in the treatment of therapy-resistant schizophrenia.

In general, the phenothiazines (e.g., chlorpromazine) and the butyrophenones (e.g., haloperidol) constitute the classical neuroleptics used in the treatment of schizophrenia to which the treatment-resistant patient does not respond. More effective pharmacotherapy for the treatment of treatment-resistant schizophrenia has not been developed in the more than three decades since the introduction of the first effective neuroleptic drugs.

Thus far, the only drug approved for clinical use in treating therapy-resistant schizophrenic patients is clozapine, which was approved by the FDA in September 1989 for this particular use. Clozapine, belonging to the class of dibenzodiazepines, was developed by 1966. Agranulocytosis, a potentially fatal drop in white blood cells, is a very dangerous side effect which occurs in 1 to 2 percent of patients treated with clozapine. Because of this harmful side effect, clozapine has not been used in many countries and for a time was withdrawn from clinical research (*Psychopharmacology*, 1989, Supplement to Vol. 99).

The fact that clozapine has now been accepted by the FDA for the treatment of therapy-resistant schizophrenic patients despite the occurrence of such serious adverse side effects, underlines the urgent need for alternative drugs to treat therapy-resistant schizophrenic patients. Moreover, there is a need for a method of treating these patients with a drug that does not give rise to potentially fatal adverse reactions.

SUMMARY OF THE INVENTION

It has now unexpectedly been found that amperozide, N-ethyl-4-[4',4'-bis(p-flurophenyl)butyl]-1-piperazinecarboxamide, a psychotropic drug developed in the late 1970s by Bjork et al (U.S. Pat. No. 4,308,387), is effective in the treatment of patients suffering from therapy-resistant schizophrenia. Amperozide has been found to be both chemically and pharmacologically different from clozapine, the only drug presently approved for the treatment of therapyresistant schizophrenia.

DETAILED DESCRIPTION OF THE INVENTION

Neuroleptic drugs reduce psychotic symptoms. However, treatment-resistant schizophrenic patients do not respond to typical neuroleptic drugs. Once treatment with two or more of the standard neuroleptic drugs has been tried and failed, the illness is defined as treatment-resistant schizophrenia.

Amperozide (N-ethyl-4-[4',4'-bis(pl)butyl]-1-piperazine-carboxamide) is effective in treating therapy-resistant schizophrenia. Amperozide may be effective in a certain subpopulation of the treatmentresistant patients due to its chemical structure and pharmacological properties.

While the mechanism by which amperozide acts to reduce the symptoms of schizophrenia remains unknown, research indicates the drug has a high affinity for serotonin-2 receptors (Svartengren and Simonsson, *Pharmacology and Toxicology*, Supplement 1, 1990, p. 8–11).

Amperozide, N-ethyl-4-[4',4'-bis(p-flurophenyl)-butyl]-1-piperazine-carboxamide, differs from clozapine and other anti-psychotic agents in possessing potent anti-aggressive and anxiolytic-like properties without causing sedation and impairment of motor control.

Amperozide has the following structural formula:

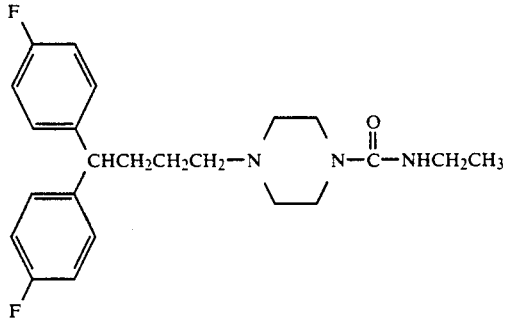

Amperozide may be a free base or an acceptable acid salt thereof such as amperozide hydrochloride. Formulations that could be used according to the present invention are disclosed in U.S. Pat. No. 4,385,057, col. 11, which is hereby incorporated by reference.

A therapeutically effective amount of amperozide for use in the treatment of therapy-resistant schizophrenia would be from about 1 to about 50 mg or possibly higher depending upon the specific condition to be treated, the age and weight of the specific patient, and the specific patient's response to the medication. Daily dosages should preferably range from 5 to 20 mg of amperozide. The exact individual dosage, as well as the daily dosage, will be determined according to standard medical principles under the direction of a physician. The preferred daily dosage is that minimal dose which causes a significant reduction in psychopathology as determined by clinical improvement or a reduction in BPRS score.

The active ingredient, amperozide, may be administered to a patient in need of such treatment according to usual routes of administration and in usual forms. These include solutions, suspensions, emulsions, tablets, capsules, and powders prepared in pharmaceutically acceptable carriers for oral administration or sterile solutions for parenteral administration.

Various additives to enhance the stability or ease of administration of the drug are contemplated. The pharmaceutical composition may also contain additional therapeutically useful substances other than amperozide.

The following examples are intended to illustrate the present invention without limiting the scope thereof.

EXAMPLES

Example 1: Preparation of an Amperozide Tablet

Amperozide tablets were prepared having the following composition:

| | | |
|---|---|---|
| Amperozide hydrochloride | 5.0 | mg |
| Lactose | 105.5 | mg |
| Microcrystalline cellulose | 13.0 | mg |
| Sodium Starch Glycolate | 5.2 | mg |
| Silicone Dioxide | 0.65 | mg |
| Magnesium Stearate | 0.65 | mg |

This core composition was coated with a conventional sucrose coating.

EXAMPLE 2: Clinical Trial of Amperozide in Treatment-Resistant Schizophrenic Patient Ten patients diagnosed as suffering from treatment-resistant schizophrenia by their resistance to classical neuroleptics were selected for this study. Amperozide, given as tablets prepared as described for Example 1 were administered daily at dosages of up to 20 mg of the active ingredient, amperozide. The patients were kept under active medication for a period of 4 weeks.

The Brief Psychiatric Rating Scale (BPRS) (Overall and Gorham, *Psychol. Rep.* 10:799-812, 1962) was used to evaluate the effect of amperozide on the psychosis of the treated patients.

In the patient population, 7 (70 percent) out of 10 treatment-resistant patients responded to the amperozide treatment. The BPRS total score was reduced by 60 percent. The positive (e.g., hallucinatory behavior and conceptual disorganization) and negative (e.g., emotional withdrawal and motor retardation) symptoms were reduced by 58 percent and 59 percent, respectively.

In comparison to clozapine (Kane, J. et al, Arch. *Gen. Psychiatry*, 1988, 45:789-796), amperozide was found to be superior both in the response rate and the onset of therapeutic effect.

Having described the invention above, various modifications of the techniques, procedures, material and equipment will be apparent to those in the art. It is intended that all such variations within the scope and spirit of the appended claims be embraced thereby.

We claim:

1. A method of treating a human suffering from therapy-resistant schizophrenia comprising administering to the human a therapeutically effective amount of amperozide, N-ethyl-4-[4',4'-bis-(p-flurophenyl) butyl]-1-piperazine-carboxamide of the formula:

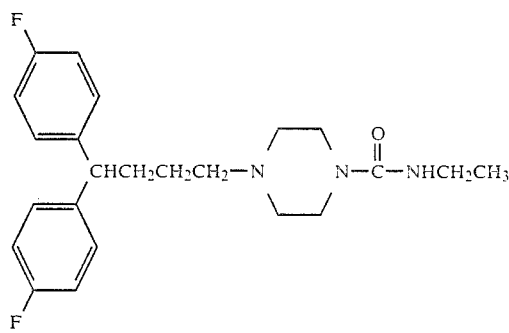

or an acceptable acid salt thereof.

2. The method of claim 1, wherein the effective amount of amperozide is dispersed within a pharmaceutically acceptable carrier.

3. The method of claim 1, wherein said therapeutically effective amount of amperozide is from about 1 to about 50 mg per day.

4. The method of claim 1, wherein said therapeutically effective amount of amperozide is from about 5 to about 20 mg per day.

* * * * *